(12) United States Patent
Collins et al.

(10) Patent No.: US 7,285,106 B2
(45) Date of Patent: Oct. 23, 2007

(54) HEMODIAFILTRATION/HEMOFILTRATION CARTRIDGES

(75) Inventors: Gregory R. Collins, Monroe, NY (US); James Summerton, Hillsdale, NJ (US); Edward Spence, Bronx, NY (US)

(73) Assignee: Nephros, Inc., New York, NY (US)

( * ) Notice: Subject to any disclaimer, the term of this patent is extended or adjusted under 35 U.S.C. 154(b) by 586 days.

(21) Appl. No.: 10/433,847

(22) PCT Filed: Dec. 11, 2001

(86) PCT No.: PCT/US01/47541

§ 371 (c)(1), (2), (4) Date: Jan. 16, 2004

(87) PCT Pub. No.: WO02/47785

PCT Pub. Date: Jun. 20, 2002

(65) Prior Publication Data

US 2004/0127842 A1     Jul. 1, 2004

Related U.S. Application Data

(60) Provisional application No. 60/254,741, filed on Dec. 11, 2000.

(51) Int. Cl.
*A61M 37/00* (2006.01)
*C02F 1/44* (2006.01)
*B01D 24/00* (2006.01)
*B01D 25/00* (2006.01)
*B01D 33/00* (2006.01)
*B01D 33/06* (2006.01)

(52) U.S. Cl. .................. 604/5.04; 604/4.01; 604/5.01; 210/646; 210/321.64; 210/321.72; 210/321.8; 210/321.81

(58) Field of Classification Search ............... 604/4.01, 604/5.01–5.04, 6.01, 6.09, 6.1, 6.11; 210/645–46, 210/321.6, 321.64, 321.72, 321.79, 321.8, 210/321.81, 321.88, 321.89, 321.9, 456
See application file for complete search history.

(56) References Cited

U.S. PATENT DOCUMENTS

| 4,498,990 A | 2/1985 | Shaldon et al. |
| 4,861,485 A | 8/1989 | Fecodini |

(Continued)

FOREIGN PATENT DOCUMENTS

| FR | 1470075 | 4/1977 |

(Continued)

OTHER PUBLICATIONS

International Search Report.

(Continued)

*Primary Examiner*—Patricia M. Bianco
(74) *Attorney, Agent, or Firm*—Darby & Darby

(57) ABSTRACT

A hemodiafiltration/hemofiltration cartridge is preferably formed of a single cartridge providing multi-stage hemofiltration and hemodiafiltration defined by a first hemodiafiltration stage having first filtering elements and a second hemofiltration stage having second filtering elements. Both stages are contained in a single cartridge. The cartridge can be used in a mid-dilution scheme, a pre-dilution scheme or a post-dilution scheme.

17 Claims, 3 Drawing Sheets

U.S. PATENT DOCUMENTS

| | | |
|---|---|---|
| 5,194,157 A | 3/1993 | Ghezzi et al. |
| 6,303,036 B1 | 10/2001 | Collins et al. |
| 6,315,895 B1 * | 11/2001 | Summerton et al. ....... 210/96.2 |
| 6,719,907 B2 * | 4/2004 | Collins et al. .............. 210/646 |
| 2006/0041216 A1 * | 2/2006 | McLaughlin et al. ...... 604/6.09 |

FOREIGN PATENT DOCUMENTS

| | | |
|---|---|---|
| JP | 50-20989 | 3/1975 |
| JP | 58-212452 | 12/1983 |
| JP | 61-276563 | 12/1986 |
| JP | 2002-521162 | 7/2002 |
| JP | 2003-518996 | 6/2003 |
| WO | WO-00/06292 | 2/2000 |
| WO | WO-01/49399 | 7/2001 |

OTHER PUBLICATIONS

Japanese Office Action for Application No. 2002-549351, dated May 30, 2006.

* cited by examiner

US 7,285,106 B2

HEMODIAFILTRATION/HEMOFILTRATION CARTRIDGES

CROSS REFERENCE TO RELATED APPLICATION

This is a U.S. national phase application under 35 U.S.C. §371 of International patent application Serial No. PCT/US01/47541, filed Dec. 11, 2001 and claims the benefit of U.S. provisional application Ser. No. 60/254,741, filed Dec. 11, 2000, which is hereby incorporated by reference in its entirety. The International application was published in English on Jun. 20, 2002 as WO 02/47785 A1 under PCT Article 21(2).

FIELD OF THE INVENTION

The present invention relates to hemodiafiltration/hemofiltration devices and methods and, more particularly, to an improved hemodiafiltration/hemofiltration cartridge and its method of use.

BACKGROUND OF INVENTION

Current treatment for End Stage Renal Disease (ESRD) essentially consists of a hemodialysis process, wherein blood to be cleaned flows on one side of a semipermeable membrane and a physiologic solution (e.g., a dialysate) flows on the other side of the membrane, whereby toxins in the blood are transferred from one side to the other. The primary driving force in this treatment is diffusion. This process is generally effective in removing small Molecular Weight (MW) toxins such as urea and creatinine. However, this process is much less effective in removing middle range MW substances, e.g., substances having a molecular weight higher than about 1 kDa, because of a low diffusion coefficient of such substances.

To a much lesser extent hemofiltration is used as a treatment modality. As in hemodialysis, the blood flows on one side of the semipermeable membrane, however, there is no dialysate flow on the other side. Instead a pressure gradient is established across the membrane so that a portion of the blood plasma water is filtered across. With the plasma water, toxins are convectively removed from the blood. Sterile non-pyrogenic replacement fluid is added to the blood either prior to or after it enters a hemofilter. The replacement fluid replaces the plasma water which is filtered across the semi-permeable membrane during the hemofiltration process. This process is generally less efficient at removing the small MW toxins compared to dialysis, but more efficient at removing the middle MW substances.

Hemodiafiltration combines dialysis and hemofiltration. Dialysate fluid flows on the other side of the semi-permeable membrane resulting in diffusion of toxins. At the same time, a pressure gradient across the membrane is maintained resulting in a high filtration rate. As with hemofiltration, sterile non-pyrogenic replacement fluid is added to the blood either prior to or after it enters a hemodiafiltration cartridge. As a result of this combination, hemodiafiltration is efficient at removing small molecules, e.g., creatinine and urea, by diffusion as well as removing large quantities of middle range MW substances, by convection.

State of the art designs for hemodiafiltration filters are substantially equivalent to those of high flux dialyzers. Such filters consist of a bundle of hollow fibers in a cylindrical housing. During operation of the hemodiafiltration system, replacement fluid is injected into the blood either upstream (pre-dilution) or downstream (post-dilution) of the high flux dialyzer.

Diafiltration devices using pre-dilution or post-dilution schemes have inherent efficiency limitations. Pre-dilution schemes allow for relatively unlimited filtration, however, because the blood is diluted prior to reaching the filter, the overall mass transfer of small solutes by diffusion is decreased. Post-dilution schemes have the advantage of keeping blood toxin concentrations high, resulting in more efficient diffusion and convection of solutes, however, the increased concentration of blood cells and the resultant higher blood viscosity during filtration, poses a limit on the amount of plasma water that can be filtered. Even the existing multistage paired filtration dialysis system disclosed in U.S. Pat. No. 5,194,157 faces the same filtration limitations due to its design.

SUMMARY OF INVENTION

It is an object of the applicants to provide a hemodiafiltration/hemofiltration cartridge that enables a higher toxin removal rate and higher toxin removal efficiency than that of prior art hemodiafiltration devices. The present cartridge reduces and/or eliminates the above-mentioned drawbacks of prior art hemodiafiltration devices by providing a scheme in which blood is diluted after it is partially, but not fully, diafiltered. The present invention combines the benefits of pre-dilution schemes, e.g., high filtration rate, with the benefits of post dilution schemes, e.g., high diffusive and convective efficiencies. The cartridge according to one embodiment can be adapted to operate in conjunction with conventional diafiltration machines, including but not limited to Fresenius 4008 On-Line Plus, Gambro AK 200 Ultra. Alternatively, the cartridge can be used with a conventional hemodialysis machine, including but not limited to, Fresenius 2008H, Baxter SPS 1550, Cobe Centry System 3, etc, that utilizes sterile replacement fluid from an externally supplied source, such as flexible bags containing normal saline or Ringer's lactate or a central delivery system as described in *Centralized on-line hemodiafiltration system utilizing purified dialysate as substitution fluid*, Sato & Koga, Artif Org 22:285, 1998. Furthermore, a standard machine may be modified to provide a source of replacement fluid, e.g., a pump or valve that meters dialysate from a tee in the main dialysate stream and passes it through a series of sterilization filters, for example as in *Influence of convection on small molecule clearances in on-line hemodiafiltration*, Ficheux, et al., Kid Int. 57:1755, 2000.

A hemodiafiltration/hemofiltration cartridge in accordance with one exemplary embodiment has blood and dialysate inlet and outlet ports. The cartridge includes a single cartridge body, for example, a cylindrical housing, with an internal separating wall which partitions the housing into first and second compartments with the first compartment being associated with a first filtration stage and the second compartment being associated with a second filtration stage. The first filtering stage communicates with the blood inlet and the second filtering stage communicates with the blood outlet. Accordingly, the hemodiafiltration/hemofiltration cartridge accomplishes diafiltration and hemofiltration within a single housing by disposing first filtering elements (a first bundle of hollow fibers) in the first compartment and second filtering elements (a second bundle of hollow fibers) in the second compartment. The present cartridge thus has the appearance of a traditional dialyzer with the exception that the dialysate ports are located on opposite sides of the cartridge. The blood inlet and blood outlet ports are preferably located at or near a first end of the cartridge. The blood inlet and outlet may be in the form of two separate caps or a single cap separated by an internal wall or seal which segregates the two filtering elements into a first hemodiafiltration stage and a second hemofiltration stage.

According to one exemplary embodiment, blood enters the blood inlet of cartridge and flows through the first filtering elements disposed within the first compartment (first stage) to an inter-stage connector disposed at an opposite second end of the cartridge. The inter-stage connector permits the blood to flow from the first filtering elements to the second filtering elements and then to the blood outlet of the cartridge. The dialysate outlet is preferably also located at or near the first end of the cartridge and communicates with the second compartment. The dialysate enters through the dialysate inlet port into the first compartment and flows counter-current to blood flow within the filtering elements of the first stage. The dialysate is drawn across a restrictive orifice in the separating wall between the first compartment and second compartment as it exits through the dialysate outlet port.

According to the one embodiment, the first stage is thus a hemodiafiltration stage and the second stage is a hemofiltration stage, both being formed in the single cartridge. In yet another embodiment, the first stage is still a hemodiafiltration stage and the second stage is a hemofiltration stage; however, the cartridge is used in either a pre- or post-dilution scheme in which replacement fluid (substitution fluid), in the pre-dilution scheme, is added to the blood to dilute the blood prior to the blood undergoing hemodiafiltration in the first stage or replacement fluid, in the post-dilution scheme, is added after the blood has undergone hemofiltration in the second stage.

Other features and advantages of the present invention will be apparent from the following detailed description when read in conjunction with the accompanying drawings.

DETAILED DESCRIPTION OF PREFERRED EMBODIMENTS

Figure 1:
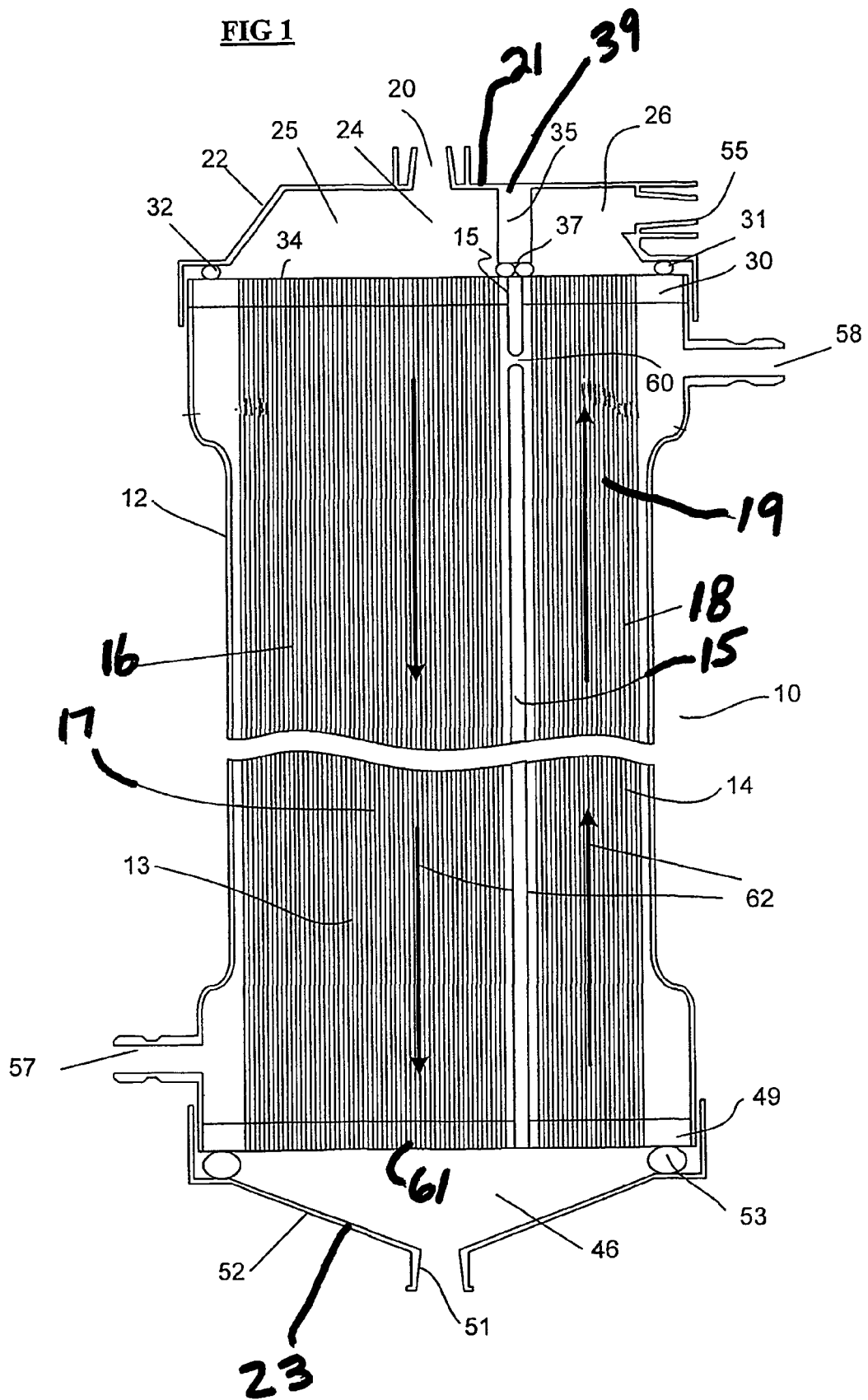
FIG. 1 is a cross-sectional illustration of a mid-dilution hemodiafiltration/hemofiltration cartridge in accordance with a first embodiment.

Reference is made to FIG. 1 which schematically illustrates a cross-sectional view of a mid-dilution hemodiafiltration/hemofiltration cartridge 10 in accordance with one exemplary embodiment. Cartridge 10 includes a cartridge body 12 which defines a first stage 13 and a second stage 14, as will be described in greater detail hereinafter. Cartridge body 12 is preferably formed of a rigid plastic material. The cartridge body 12 is partitioned into first and second internal compartments 17, 19, respectively, by an inner wall 15. Preferably the inner wall 15 is made of the same rigid material that is used to make the cartridge body 12 and the inner wall 15 may be integrally formed with the cartridge body 12 (e.g., as part of a molded member). As will be described in greater detail hereinafter, the first compartment 17 generally corresponds to the first stage 13 and the second compartment 19 generally corresponds to the second stage 14.

Disposed within cartridge body 12 are longitudinal bundles of semi-permeable hollow fibers which are divided into first and second longitudinal bundles 16, 18. More specifically, the first longitudinal bundle of semi-permeable hollow fibers 16 is disposed within the first compartment 17 and the second longitudinal bundle of semi-permeable hollow fibers 18 is disposed within the second compartment 19. The semi-permeable hollow fibers 16, 18 serve as a means for transferring the toxins which are being filtered from blood. The semi-permeable hollow fibers 16, 18 can be of any type suitable for this type of application and are commercially available from a number of sources. The semi-permeable hollow fibers 16 can be referred to as arterial fibers and the semi-permeable hollow fibers 18 can be referred to as venous fibers.

In one exemplary embodiment, cartridge 10 is adapted to operate in conjunction with a hemodiafiltration machine, such as the Fresenius 4008 On-Line Plus or Gambro AK200 Ultra or a modified hemodialysis machine, such as the Fresenius 2008H, Cobe Centry System 3, or Baxter SPS 1550.

During operation, blood transferred from the patient, via a blood pump and bloodlines (not shown), enters the first stage 13 of cartridge 10 through an inlet port 20, which is preferably integrally formed in a header cap 22 mounted at a first end 21 of the cartridge 10. The header cap 22 defines an inner header space 24 which is actually divided into a first inner header space 25 and a second inner header space 26. The first inner header space 25 may be referred to as an arterial blood space and the second inner header space 26 may be referred to as a venous blood space. As will be explained in greater detail hereinafter, the first and second inner header spaces 25, 26 are associated with the first and second stages 13, 14 (first and second compartments 17, 19, respectively).

Both the first and second inner header spaces 25, 26 may be separated from the rest of the cartridge 10 by a first potting compound 30, which forms a seal around the outside surfaces of the semi-permeable hollow fibers 16, 18 at the first end 21 of the cartridge body 12. The header cap 22 can be removable and, in such case, the first and second inner header spaces 25, 26 are preferably sealed from the external environment and each other by sealing members, such as O-rings 31, 32. As shown, the O-ring 32 is associated with the first compartment 17 and the O-ring 31 is associated with the second compartment 19.

Blood enters the first inner header space 25 through the inlet port 20, and then enters the semi-permeable hollow fibers 16 at an interface 34. The interface 34 preferably includes a potting compound (e.g., polyurethane) interface structure. The first inner header space 25 may be separated from the second inner header space 26 by several techniques. For example, as illustrated in FIG. 1, the first inner header space 25 may be separated from the second inner header space 26 by an internal wall 35 which partitions the inner header space 24 into the first and second spaces 25, 26. Preferably, the internal wall 35 is formed as an integral part of the header cap 22. The internal wall 35 seals against the O-rings 31, 32 effectively eliminating any blood communication between the two header spaces (first and second inner header spaces 25, 26). In the illustrated embodiment, the O-rings 31, 32 are disposed at a distal end 37 of the internal wall 35 opposite a proximal end 39 of the internal wall 35 which attaches to or extends from the header cap 22. The O-rings 31, 32 thus provide a sealing action when the header cap 22 interfaces with the interface 34.

The semi-permeable hollow fibers 16 in the first compartment 17 (first stage 13) communicate with the first inner header space 25 and the semi-permeable hollow fibers 18 in the second compartment 19 (second stage 14) communicate with the second inner header space 26. The two fiber bundles 16, 18 are separated by the inner wall 15. The ends of the inner wall 15 can become encased in the interface 34 during the fiber bundle potting process.

As blood enters the first inner header space 25 through the inlet port 20, the blood traverses down the inside of the arterial fibers 16 (first fiber bundle), along a filtration space of the first compartment 17 of the first stage 13, with the outsides of the arterial fibers 16 being immersed in a flowing stream of dialysate fluid through the first internal compartment 17. The pressure of the dialysate fluid in the first internal compartment 17 is less than the pressure of the blood flowing through the inside of the arterial fibers 16 such that a forward filtration of blood plasma water occurs across the semi-permeable membrane (arterial fibers 16) from the bloodside to the dialysate side of the first filtration stage 13. This results in first stage hemodiafiltration of toxins, i.e., both filtration and diffusion, which takes place along the entire length of the arterial fibers 16 within the first compartment 17. According to one embodiment, a significant portion, e.g., approximately about 20%-60%, of the plasma water is preferably filtered across the semi-permeable membrane as the blood flows through the first stage 13. Partially hemodiafiltered blood exits the arterial fibers 16 and enters an inter-stage connector (header space) 46 associated with another end 23 of the cartridge 10. As used herein, the term "partially hemodialfiltered" refers to blood that has undergone a hemodiafiltration process, which causes some of the toxins contained in the blood to be removed therefrom.

The blood entering the inter-stage header space 46 is in a hemoconcentrated state relative to the blood entering the cartridge 10 at the blood inlet 20, i.e., the hematocrit of the blood entering the inter-stage space 46 is greater than that at the blood inlet 20. The first compartment 17 of the first stage 13 and the second compartment 19 of the second stage 14 are preferably separated from the inter-stage header space 46, for example, by a second potting compound 49. Thus, the second potting compound 49 forms a second interface 61.

The inter-stage header space 46, which acts as a transition stage for blood exiting the first stage 13 and entering the second stage 14, is defined by a second header cap 52 which is preferably made from rigid plastic material and is attached to the second end 23 of the cartridge body 12. The inter-stage header space 46 can be sealed from the external environment with a third O-ring 53. As shown in FIG. 1, the third O-ring 53 is disposed between the second potting compound 49 and the second header cap 52, thereby producing a seal therebetween. In one embodiment, the first and second header caps 22, 52 are of a detachable type in that each can be easily coupled to and removed from the cartridge body 12. For example, the cartridge body 12 and the first and second header caps 22, 52 can contain complementary threads for threadingly coupling to one another.

The blood residing in the inter-stage header space 46 prior to entering the second stage 14, is diluted with a physiological sterile solution that enters cartridge 10 via a header inlet port 51. The sterile solution can be produced continuously, in an "on-line" manner, or provided from reservoirs, e.g., saline bags, as are known in the art. The blood in the inter-stage header space 46 is hemodiluted relative to the blood entering the cartridge 10 at the blood inlet 20, i.e., the blood hematocrit level becomes less than that of the blood at the blood inlet 20.

The hemodiluted blood then enters the venous fibers 18, disposed in the second stage 14, and is then carried by the venous fibers 18 toward the first end 21 of the cartridge 10. The pressure of the hemodiluted blood traversing through the venous fibers 18 is at an elevated pressure relative to the fluid pressure inside the second internal compartment 19 that resides on the outside of the venous fibers 18, such that a forward filtration of blood plasma water (hemofiltration) occurs across the semi-permeable membrane (venous fibers 18) from the bloodside to the dialysate side of the second filtration stage 14. The volume of blood plasma water filtered from the hemodiluted blood as it flows through the second filtering stage is such that the hemocrit of the blood exiting the cartridge 10 at the blood outlet 55 is substantially equal to the hematocrit at the blood inlet 20 with the exception that some small differences may be necessary as a means to control net ultrafiltration for maintenance of patient fluid balance. The plasma water that is filtered across the second filtering stage 14 flows toward the dialysate outlet 58 and is discharged from the cartridge 10 along with the spent dialysate flowing through the restrictive orifice 60 from the first filtration stage 13. Hemofiltration thus takes place along the length of these venous fibers 18 until the blood exits into the second inner header space 26 (venous space) of the first header cap 22 and out of an outlet port 55 formed in the first header cap 22. The outlet port 55 is therefore referred to as a venous port. The venous port 55 may be of the same type as the inlet port 20, e.g., a standard twist lock connector. It will be appreciated that the venous port 55 may be formed of another type of connector.

From an external view, the dialysate flow and connections are similar to those in standard dialysis processes. However, the internal dialysate flow actually serves to regulate the relative filtration rates between the two stages. Dialysate enters the cartridge 10 through a dialysate inlet port 57, e.g., a standard Hansen connector as is known in the art. The dialysate fluid in the present invention perfuses and flows through the first internal compartment 17 around the outside of the first stage semi-permeable hollow fibers 16. The dialysate fluid exits the cartridge 10 through a dialysate exit port 58 located on the opposite side of the wall 15 near the first potting compound 30 of the second stage 14. Preferably, the dialysate inlet port 57 and the dialysate exit port 58 are the same type of port, e.g., Hansen connector.

In an embodiment of the present invention, the dialysate fluid runs counter-current to the blood in the first stage 13. As it nears the first end 21 of the cartridge 10, the dialysate fluid is drawn across a hole or orifice 60 formed in the separating wall 15. The orifice 60 thus provides fluid communication between the first internal compartment 17 (first stage 13) and the second internal compartment 19 (second stage 14). The dimension of the orifice 60 may be varied depending upon the precise application and other parameters. The dialysate is then drawn out of the dialysate exit port 58 which is associated with the second stage 14. Preferably, the orifice 60 is located proximate to the dialysate exit port 58 so that there is effectively minimal dialysate flow in the second (hemofiltration) stage 14. More specifically, the orifice 60 is preferably generally aligned with the dialysate exit port 58 so that the dialysate fluid simply flows across the second compartment 19 to the dialysate exit port 58 where the dialysate fluid exits.

Filtration takes place from the blood to the dialysate across the semi-permeable walls of the hollow fibers 16, 18. The overall filtration rate is a function of the dialysate fluid outflow and replacement fluid inflow and advantageously is significantly greater than is achievable in conventional post-dilution hemodiafiltration. According to one embodiment, the overall filtration rate is preferably from about 25% to about 85%, more preferably from about 40% to about 60% of the blood flow rate. These flows may be controlled by pumps within a conventional hemodiafiltration machine (not shown).

The relative filtration rates of the first and second stages 13, 14 are controlled by the relative balance of transmembrane pressure (TMP) between the blood compartments and the filtrate compartments. The blood side pressure is a function of the blood flow rate and the blood viscosity within each blood compartment (which is a function of the degree of hemoconcentration and hemodilution in each of the blood compartments). Since the blood flows serially from the first stage 13 to the second stage 14, the pressure of the blood in the first stage 13 is greater than the pressure of blood in the second stage 14. In a typical dialysis machine, the dialysate compartment pressure is controlled by a pump downstream of the dialysate outlet. For this embodiment, the pressure of the internal compartment 19 outside the venous fibers 18 of the second stage 14 is controlled in this manner. The pressure of the internal compartment 17 (first compartment) outside the arterial fibers 16 of the first stage 13 is primarily a function of the dialysate fluid outlet pressure 58, the flow rate of dialysate fluid through the orifice 60, the viscosity of the dialysate fluid, and the size of the orifice 60 between the two stages. In approximate terms, the dialysate fluid pressure in the first compartment 17 is higher than the dialysate fluid pressure in the second compartment 19 by an amount equal to the pressure drop or pressure loss across the inter-compartment orifice 60.

The blood in the first stage 13 is hemoconcentrated, but at high pressure, while the blood in the second stage 14, is hemodiluted and at low pressure. To maximize the total filtration of both filtration stages 13 and 14, it is desired that the dialysate compartment 17 pressure in the first stage 13 is greater than the dialysate compartment 19 pressure in the second stage 14. This is achieved through a properly sized inter-compartment orifice 60. As dialysate flows across the orifice 60 from the first compartment 17 to the second compartment 19, it undergoes a pressure drop. Thus the dialysate pressure in the first compartment 17 is higher than in the second compartment 19. For a given dialysate flow range, typically about 500-1000 ml/min, the orifice 60 can be sized to give a pressure drop that results in the desired relative filtration rates between the two stages 13, 14. For example, it can be desired to maximize the combined filtration rate of the two filtration stages 13 and 14. To accomplish this, one operates each stage at a relatively high transmembrane pressure. Since the blood pressure in the first filtration stage 13 is higher than the second filtration stage 14 by some amount dependent upon the blood flow rate, the size of the orifice 60 should be sized such that the pressure drop across the orifice 60 for a given dialysate flow rate results in the transmembrane pressure of each filtration stage being equal.

Reuse of the cartridge 10 is similar to standard dialyzers in that the blood inlet port 20 and venous port 55 and dialysate inlet and exit ports 57, 58 are connected to a reuse machine. During a reuse application, the substitution inlet port 51 is capped.

For purpose of illustration, the blood flow within the cartridge 10 according to one embodiment is indicated by arrows 62.

It will be appreciated that the cartridge body 12 and end caps 22, 52 can be integrally formed as a single member (a housing) and thus the housing will have formed therein the blood inlet 20, blood outlet 55, dialysate inlet 57 and dialysate outlet 58, as well as the inter-stage connector section that defines the inter-stage header space 46. The use of the term "end cap" is not limiting but rather is merely exemplary of one embodiment where end caps are attached to a housing body to form the complete cartridge 10. The term "housing" thus may be used to refer to the entire structure including the cartridge body 12 and the end caps 22, 52 as either an assembled member or as an integral unitary member.

Figure 2:
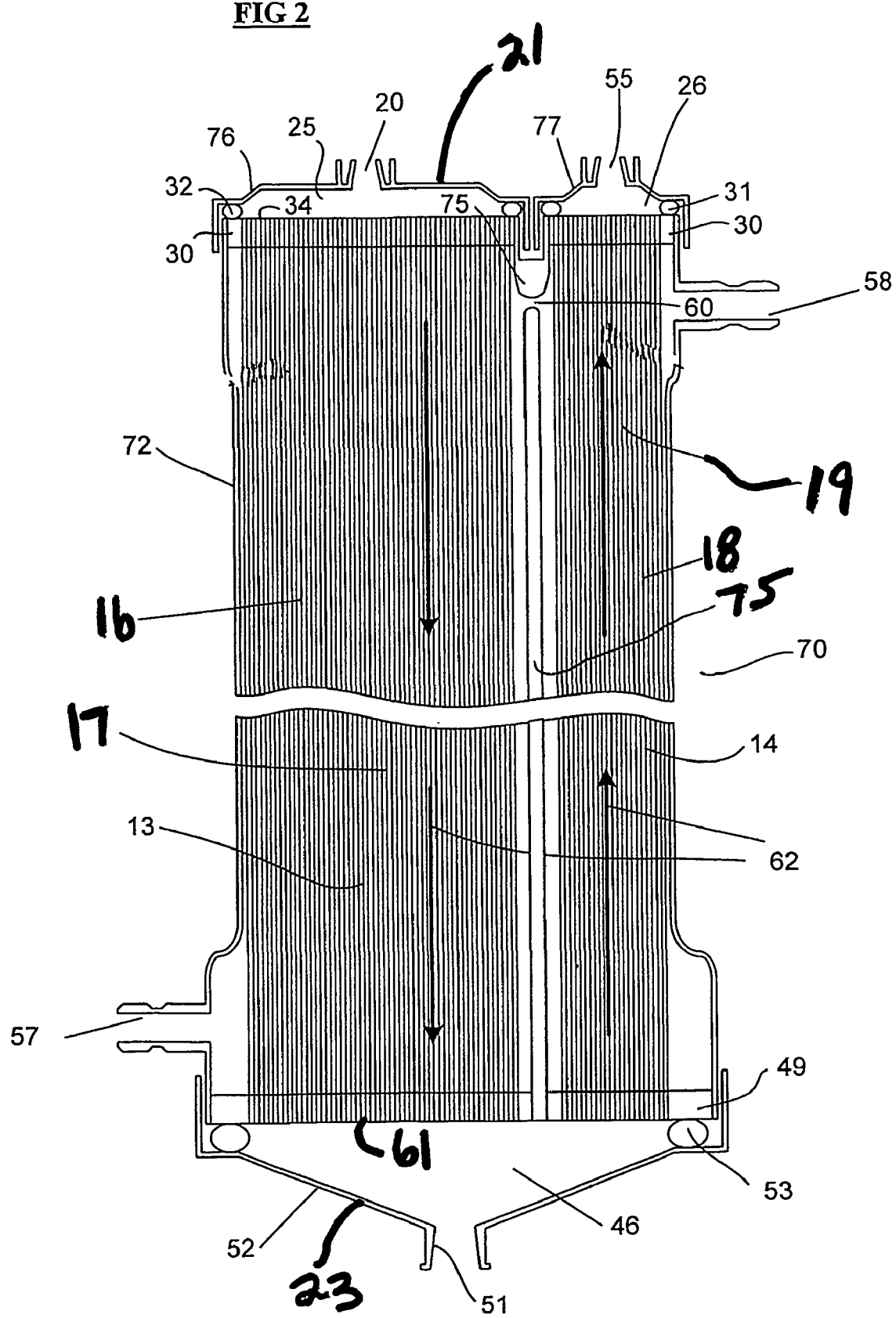
FIG. 2 is a cross-sectional illustration of a mid-dilution hemodiafiltration/hemofiltration cartridge in accordance with a second embodiment.

Reference is made to FIG. 2 which schematically illustrates a cross-sectional view of a second embodiment of a mid-dilution hemodiafiltration/hemofiltration cartridge, generally indicated at 70. The design is similar to the first embodiment with the primary change being separation of the blood inlet and outlet into separate first and second headers 76, 77 rather than one with a separating wall, as shown in FIG. 1. In this embodiment, the first header 76 may be referred to as a blood inlet header 76 and the second header 77 may be referred to as blood outlet header 77.

The cartridge 70 includes a cartridge body 72 having an internal separating wall 75 running the length of the cartridge body 72. At or near a blood inlet and outlet end (first end 21) of the cartridge body 72, the wall 75 divides into two separate walls with attachments for first and second headers 76, 77. In other words, the wall 75 has retaining features which permit the wall 75 to attach to the first and second headers 76, 77. One advantage of this second embodiment is the first and second headers 76, 77 may be easily attached and removed for manufacturing and device reuse. The cartridge 70 operates in an identical or substantially similar manner relative to the cartridge 10 of the first embodiment.

It will be understood that in another embodiment, the dialysate may be designed to flow co-current to the semi-permeable hollow fibers 16 of the first stage 13; however, the preferred embodiment where the dialysate flows counter-current to the semi-permeable hollow fibers 16 of the first stage 13 results in a more efficient removal of toxins. The counter-current flow in the first stage 13 keeps a maximum concentration gradient of uremic toxins permitting for high diffusive clearance of small molecular weight (MW) solutes. The concentration of small MW solutes at the entrance of the second stage 14 is relatively low, and any increase in clearance by diffusion would likely be minimal. However, the concentration of middle MW solutes may still be quite high after partial diafiltration. Since increased removal for both of these will primarily be by convection, dialysate flow is not required in the second stage 14. Its absence has little impact on the overall removal efficiency. Acting as a hemofilter, the second stage 14 also offers the advantage of being able to control the relative filtration rates of the first and second stages 13, 14 via the orifice 60 between the filtrate compartments 17, 19 of the two stages 13, 14 near the dialysate outlet 58.

Figure 3:
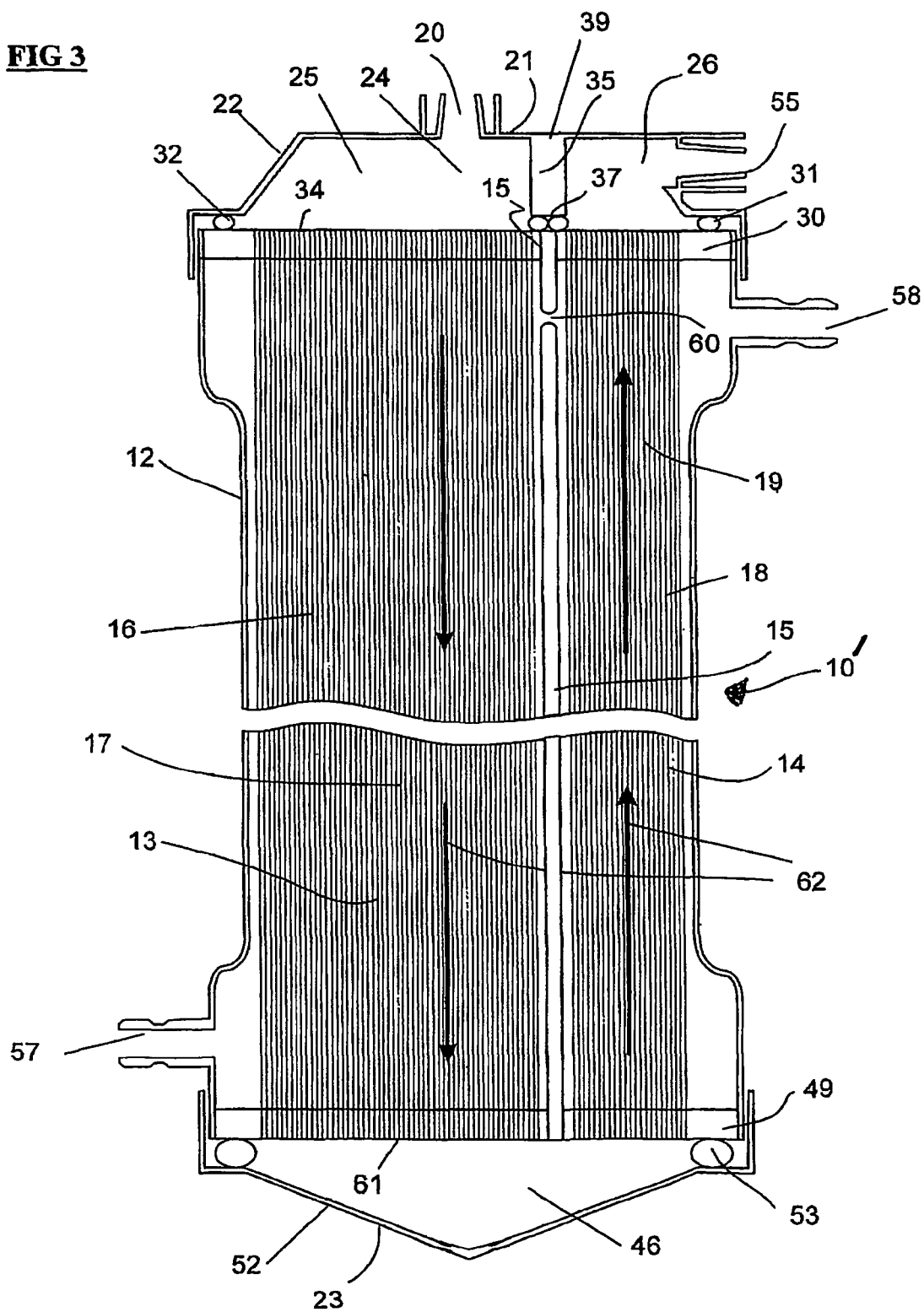
FIG. 3 is a cross-sectional illustration of a pre- or post-dilution hemodiafiltration/hemofiltration cartridge according to a third embodiment.

Now turning to FIG. 3 in which another exemplary embodiment is illustrated. In this embodiment, a cartridge 10' is provided and has essentially the same configuration as the cartridge 10 of FIG. 1 except that the cartridge 10' is not a mid-dilution hemodiafiltration/hemofiltration cartridge but rather is to be employed in either a pre-dilution scheme or a post dilution scheme. For purposes of clarity and ease of illustration, the elements of FIG. 3 that are alike as compared to FIG. 1 are numbered alike. In a pre-dilution scheme, the blood is diluted with a substitution fluid or the like prior to the diluted blood entering the blood inlet 20. The diluted blood then undergoes hemodiafiltration in the first stage 13 before flowing into the inter-stage space 46 as partially diafiltered blood. Because of a pressure differential between the first and second stages 13, 14, the partially diafiltered blood flows into the second stage 14 where it then undergoes hemofiltration as it flows within the second filtering elements 18 before finally being discharged through the blood outlet 55. The characteristics of the blood that is discharged through the blood outlet 55 in a pre-dilution scheme are preferably the same as the characteristics of the blood that is discharged through the blood outlet 55 in the mid-dilution scheme of FIG. 1 or 2.

As previously mentioned, the cartridge 10' of FIG. 3 can also be used in a post-dilution scheme. In this type of scheme, the blood enters through blood inlet 20, undergoes hemodiafiltration in the first stage 13, flows into and through the inter-stage space 46 as partially diafiltered blood and then flows into the second stage 14, where the partially diafiltered blood is subjected to hemofiltration. After undergoing hemofiltration in the second stage 14, the blood then is discharged through the blood outlet 55. The discharged blood is then diluted (e.g., substitution fluid is mixed with the discharged blood) so as to return the blood to a desired state before introducing the blood back into the patient.

It will be appreciated by persons skilled in the art that the present invention is not limited to the embodiments described thus far with reference to the accompanying drawings. Rather the present invention is limited only by the following claims.

What is claimed:

1. A mid-dilution hemodiafiltration/hemofiltration cartridge comprising:
   a cartridge body having a first end and an opposing second end, said cartridge body being in communication with a blood inlet and a blood outlet and a dialysate inlet and outlet;
   a first hemodiafiltration stage including a first filtering element disposed between said first and second ends of said cartridge body, said blood inlet communicating with said first filtering element at said first end so that blood flows through said first filtering element toward said second end;
   a second hemofiltration stage including a second filtering element disposed between said first and second ends of the cartridge body, said blood outlet communicating with said second filtering element;
   a separating wall disposed between the first and second ends of the cartridge body and partitioning the body into the first hemodiafiltration stage and the second hemofiltration stage, the separating wall including an orifice to provide communication between the first hemodiafiltration stage and the second hemofiltration stage; and
   an inter-stage connector disposed at said second end of said cartridge body and defining an inter-stage header space, said inter-stage header space permitting blood that has been discharged from said first hemodiafiltration stage to flow through said second filtering element to said blood outlet, said inter-stage connector having a substitution fluid inlet port for reception of a solution for diluting the blood prior to the blood entering said second filtering element of said second stage,
   wherein dialysate fluid enters from said dialysate inlet and flows through said first hemodiafiltration stage, through the orifice, and then flows into said second hemofiltration stage and out said dialysate outlet associated with said second hemofiltration stage.

2. The mid-dilution hemodiafiltration/hemofiltration cartridge of claim 1, wherein said first end of said cartridge body is sealed with a first header cap which has the blood inlet and blood outlet formed therein.

3. The mid-dilution hemodiafiltration/hemofiltration cartridge of claim 2, wherein said first header cap has a internal wall member for dividing an inner header space into a first header space and a second header space, wherein said first header space permits the blood to only flow from said blood inlet port to said first filtering elements of said first stage and wherein said second header space permits the blood to only flow from said second filtering elements to said blood outlet port.

4. The mid-dilution hemodiafiltration/hemofiltration cartridge of claim 3, wherein blood entering said first header space through said blood inlet is excluded from said second filtering element by said internal wall member which prevents the blood from flowing into said second header space.

5. The mid-dilution hemodiafiltration/hemofiltration cartridge of claim 1, wherein said first end of said cartridge body is seated with a first header cap, said first header cap having an internal wall member for defining a first header space and a second header space, said internal wall member being axially aligned with said separating wall.

6. The mid-dilution hemodiafiltration/hemofiltration cartridge of claim 5, wherein said internal wall member is integral to said first header cap and includes a pair of O-rings to provide a seal between said first header cap and said cartridge body at an attachment interface therebetween.

7. The mid-dilution hemodiafiltration/hemofiltration cartridge of claim 1, wherein blood flows through said first filtering element at a first fluid pressure and flows through said second filtering element at a second fluid pressure which is less than the first fluid pressure, and wherein a first compartment defining the first hemodiafiltration stage has a first associated pressure which is greater than a second associated pressure of a second compartment defining the second hemofiltration stage.

8. The mid-dilution hemodiafiltration/hemofiltration cartridge of claim 7, wherein said orifice is dimensioned so as to cause the first associated pressure to be greater than the second associated pressure.

9. The hemodiafiltration/hemofiltration cartridge of claim 1, wherein said blood inlet and said blood outlet are formed in a first header cap disposed at said first end of said cartridge body and the inter-stage connector is defined by a second header cap disposed at said second end of said cartridge body, said first header cap being configured so that said blood inlet is only in communication with said first hemodiafiltration stage and said blood outlet is only in communication with said second hemofiltration stage.

10. The hemodiafiltration/hemofiltration cartridge of claim 9, wherein said orifice is axially aligned with said dialysate outlet to limit the area of said second compartment through which the dialysate fluid flows.

11. The mid-dilution hemodiafiltration/hemofiltration cartridge of claim 1, wherein each of said first and second filtering elements comprises high flux semi-permeable hollow fibers.

12. The mid-dilution hemodiafiltration/hemofiltration cartridge of claim 1, wherein said first and second filtering elements are separated by said separating wall along their full length.

13. The mid-dilution hemodiafiltration/hemofiltration cartridge of claim 1, wherein said orifice is axially aligned with said dialysate outlet.

14. The mid-dilution hemodiafiltration/hemofiltration cartridge of claim 1, wherein said first end of said cartridge body is sealed with first and second header caps, said first header cap including the blood inlet and defining a first header space in communication only with said first filtering element, said second header cap including the blood outlet and defining a second header space in communication only with said second filtering element.

15. The mid-dilution hemodiafiltration/hemofiltration cartridge of claim 1, wherein said orifice is dimensioned so as to cause a first compartment defining said first hemodiafiltration stage to have a first dialysate pressure and a second compartment defining said second hemofiltration stage to have a second dialysate pressure which is greater than the first dialysate pressure.

16. A method of hemodiafiltration/hemofiltration in a single cartridge, the method comprising the steps of: partitioning said single cartridge into said first and second stages with a separating wall defining the two stages, the first stage including a first filtering element and the second stage including a second filtering element; receiving a blood inflow; diafiltering said blood inflow in the first stage to provide a partially diafiltered blood outflow having a first concentration of toxins; mixing said partially diafiltered blood outflow with a substitution fluid at an inter-stage section to provide a blood/substitution fluid mixture; and hemofiltering said blood/substitution fluid mixture in a second stage to produce blood having a second concentration of toxins, the first concentration being greater than the second concentration, wherein said diafiltering and said hemofiltering steps occur within said single cartridge; and passing dialysate fluid through a dialysate inlet and into said first stage, the dialysate fluid flowing within the first stage before flowing through a restrictive orifice formed in the separating wall and across a discrete area of the second stage to a dialysate outlet.

17. The method of claim 16, further including the step of: dimensioning the orifice so that an area around said first filtering elements has a first pressure and an area around said second filtering elements has a second pressure, the first pressure being greater than the second pressure.

* * * * *